United States Patent [19]

Kopp

[11] Patent Number: 4,610,682
[45] Date of Patent: Sep. 9, 1986

[54] DISPOSABLE DIAPER

[76] Inventor: Yvette B. Kopp, 6712 Villere St., Arabi, La. 70032

[21] Appl. No.: 758,691

[22] Filed: Jul. 25, 1985

[51] Int. Cl.[4] .............................................. A61F 13/16
[52] U.S. Cl. ................................................ 604/385 R
[58] Field of Search .................... 604/385.1, 385.2, 369

[56] References Cited

U.S. PATENT DOCUMENTS 3,349,769  10/1967  Piekarski ........................ 604/369 X
3,572,342   3/1971  Lindquist et al. .................. 604/369

Primary Examiner—John D. Yasko
Attorney, Agent, or Firm—James B. Lake, Jr.

[57] ABSTRACT

Fluid permeable inner facing and impermeable outer facings are biased cut with reduced width between oppositely disposed larger ends, and absorbent filler sandwiched between the facings. A strip of inner facing as long as a diaper periphery is wrapped around a rolled belt of absorbent filler and the facing edges of inner and outer facings are sewed together with the edges of the wrapped belt of filter to form a border welted edge. Fastening flaps extend from the upper part of the diaper transversely to fasten by adhesive tape to a folded up lower portion of the diaper and secure it in place.

1 Claim, 4 Drawing Figures

U.S. Patent  Sep. 9, 1986  4,610,682
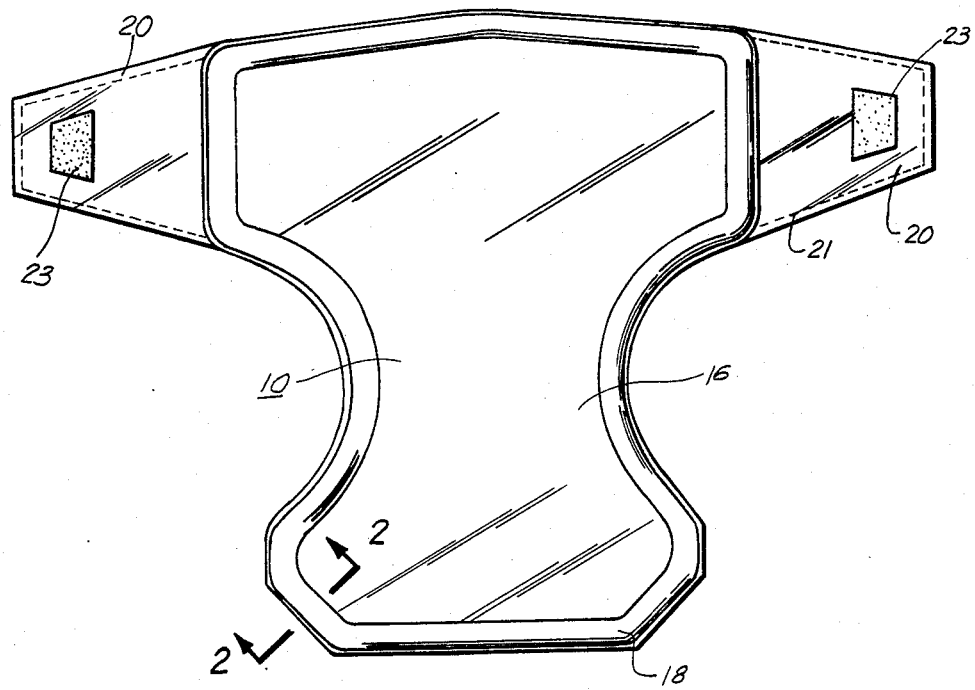
FIG. 1
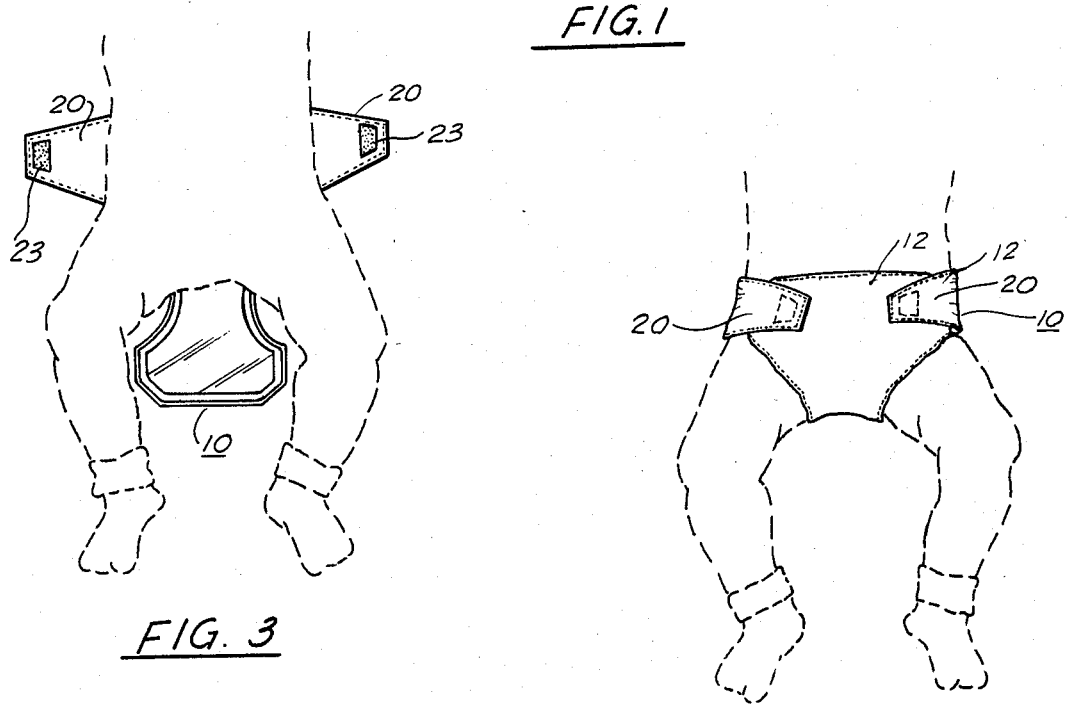
FIG. 3
FIG. 4
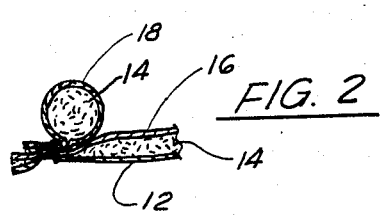
FIG. 2

DISPOSABLE DIAPER

BACKGROUND OF THE INVENTION

The invention relates generally to diapers for the young and incontinent, and more particularly to an improved disposable diaper.

The prior art discloses a disposable diaper that is elongated, rectangularly shaped, and provides a far larger amount of material between the legs of a wearer than is comfortable or necessary, and elastic cords extending along the sides of the diaper short of the ends for engaging around the legs of a wearer to prevent leakage.

The invention teaches a diaper with reduced width intermediate the ends for cutting unnecessary and uncomfortable amounts of material from the diaper extending between the legs of a wearer, that is cut on a bias to provide some elasticity for engaging around the legs of a wearer, and is provided with a welted edge that in cooperation with the bias cut elasticity prevents leakage.

SUMMARY OF THE INVENTION

It is an object of the invention to provide a disposable, less bulky, better fitting, less irritating and non-leaking diaper for the young and incontinent.

BRIEF DESCRIPTION OF THE DRAWINGS

FIG. 1 is a plan view of the invention laid out for application to a wearer;

FIG. 2 is a cross-sectional view taken along section lines 2—2 of FIG. 1;

FIG. 3 is similar to FIG. 1 with a partial figure of a baby superimposed thereon; and FIG. 4 is similar to FIG. 3 with invention in operational position.

DETAILED DESCRIPTION OF THE PREFERRED EMBODIMENT

Referring to FIGS. 1-4, the disposable diaper 10 of the invention comprises an outer moisture impermeable facing 12, an inner moisture permeable facing 16, bulk absorbent filler 14 between said facings, and a moisture retaining peripheral welted edge 18 that fixes all said components in respective operational relationship.

Outer facing 12 comprises a flexible material that is cut on a bias to provide longitudinal and transverse stretchability, and on each side to reduce diaper width intermediate its oppositely disposed ends, the upper end of which is larger both longitudinally and transversely than the lower end (see FIG. 1) and transversely extended outwardly in fastening flaps 20. Referring more particularly to FIGS. 2 and 3, absorbent filling 14 is cut similarly to the facings less the fastening flaps 20. A belt of absorbent filler is rolled between a strip of bigs cut inner facing as long as the periphery of the diaper less the fastening flaps, and the edges of the facings and the belt are sewed together to form the stretchable welted edge 18. Adhesive tape fasteners 23 are fixed to respective inner surfaces of fastening flaps 20 adjacent the oppositely disposed ends thereof.

In use, disposable diaper 10 is laid out unfolded on any convenient support (not shown) with its inner facing 16 uppermost and with its fastening flaps 20 oppositely extended. A prospective wearer is place flat on his back on said inner facing with the reduced middle width adjacent the wearer's crotch. The diaper part below said reduced width is folded up between the wearer's legs with the inner facing resting flat against his abdomen. The fastening flaps are then folded pulled inwardly over the outer facing 12 of the upwardly folded diaper end and fixed thereto by the adhesive tape fasteners 23. Said diaper is removed for disposal by reversing the process, that is by pulling the fastening flaps upwardly and outwardly, releasing the tape fasteners and then folding down the diaper part between the legs and removing it from under the wearer. Welted edge 18 prevents the escape of excess fluid or solid matter without any chance of cutting off circulation or irritating the skin as with elastics and plastics.

What is claimed is:

1. An improved disposable diaper comprising:
   (a) inner and outer facings respectively fluid permeable and impermeable cut on a bias from said materials for longitudinal and transverse stretchability, and with reduced width intermediate oppositely disposed ends for lessening diaper bulk between legs and around waist of wearer, one said outer facing end being transversely extended outwardly in opposite directions for fastening flaps;
   (b) absorbent filler sandwiched between said facings for absorbing fluid through said liquid permeable facing;
   (c) a belt of said absorbent filter wrapped in a bias cut strip of said permeable facing the length of a permeable facing periphery for fixing in a bias cut welted edge closing said facings against leakage therethrough and thereunder; and
   (d) fastening flaps extending transversely from an end of said impermeable facing for stretch folding forwardly around and over an opposite diaper end upwardly folded between the legs of said wearer with no overlapping of absorbent filler parts.

* * * * *